US000001825H

United States Statutory Invention Registration [19]

[11] Reg. Number: H1,825

Romano et al. [45] Published: Dec. 7, 1999

[54] ISOTHERMAL TRANSCRIPTION BASED ASSAY FOR THE DETECTION OF HTLV I AND HTLV II RNA

[75] Inventors: Joseph W. Romano, Derwood, Md.; Roxanne Shurtliff, Herndon; Kimberly G. Williams, Falls Church, both of Va.

[73] Assignee: Akzo Nobel N.V., Arnhem, Netherlands

[21] Appl. No.: 09/015,876

[22] Filed: Jan. 30, 1998

[51] Int. Cl.[6] ..... C12Q 1/68

[52] U.S. Cl. ..... 435/6

[56] References Cited

U.S. PATENT DOCUMENTS 5,234,809 8/1993 Boom et al. .
5,409,818 4/1995 Davey et al. .
5,554,517 9/1996 Davey et al. .

OTHER PUBLICATIONS

B. Srivastava et al., *Cancer Research*, 52:4391–4395, 1992.
D. Zucker–Franklin et al., *AIDS Res. and Hum. Retroviruses*, 10:9:1173–77, 1994.
J. Romano et al., *Immunological Investigations*, 26(1&2):15–28, 1997.
H. Poteat et al., *Journal of Virology*, 63:4:1604–1611, 1989.
Frey et al., *Schweizer Archiv Für Tierheilkunde*, 138:3:121–124, 1996.
W. Hall et al., *Science*, 253:317–320, 1991.
J. Blomberg et al., *Journal of AIDS*, 5:294–302, 1992.
Bazarbachi et al., *Science*, 259:1470–1471, 1993.
N. Manca et al., *J. Exp. Med.*, 180:1973–1978, 1994.
P. Tuke et al., *Journal of Virological Methods*, 40:163–174, 1992.
R. Grassmann et al., *Proc. Natl. Acad. Sci. USA*, 86:3351–3355, 1989.
J. Green et al., *Nature*, 341:72–74, 1989.
V. Kalyanaraman et al., *The EMBO Journal*, 4:6:1455–1460, 1985.
E. DeFreitas et al., *Proc. Natl. Acad. Sci. USA*, 88:2922–2926, 1991.
V. Kalyanaraman et al., *Science*, 218:571–573, 1982.
Z. Berneman et al., *Proc. Natl. Acad. Sci. USA*, 89:3005–3009, 1992.

*Primary Examiner*—Charles T. Jordan
*Assistant Examiner*—Meena Chelliah
*Attorney, Agent, or Firm*—Mary E. Gormley

[57] ABSTRACT

An isothermal transcription based amplification assay for the detection of HTLV I RNA uses primers and probes for sequences within the tax gene, the pol gene, or the gag gene. An isothermal transcription based amplification assay for the detection of HTLV II uses primers and probes for sequences within the tax gene. Target specific primers and probes are also disclosed.

21 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ISOTHERMAL TRANSCRIPTION BASED ASSAY FOR THE DETECTION OF HTLV I AND HTLV II RNA

FIELD OF THE INVENTION

The present invention is directed to an isothermal transcription based assay for the detection of HTLV I and HTLV II RNAs. The present invention is also directed to oligonucleotides for amplifying HTLV I and HTLV II RNA and probes for use in the detection of the amplification product.

BACKGROUND OF THE INVENTION

Human T-cell lymphotropic virus type I (HTLV I) has been identified as the etiological agent responsible for adult T-cell leukemia/lymphoma (ATLL). It has also been associated with a chronic neurological disorder known as tropical spastic paraparesis (TSP) or HTLV-associated myelopathy (HAM) (Reitz et al., 1983, *J. Infect. Dis.* 147:399–405; Gessain et al., 1985, *Lancet,* ii:407–410). The virus can be transmitted by blood transfusion, intravenous drug abuse, sexual contact and through breast feeding, and infection is endemic in southwestern Japan, Central Africa, and in parts of the Caribbean. The virus has also been found in North America and Europe.

The closely related human T-cell lymphotropic virus type II (HTLV II) is not definitely implicated in human disease, although it has been identified in two cases of atypical hairy cell leukemia (Kalyanaraman et al, 1982, *Science,* 218:571–573), HTLV II-like sequences have been detected in patients with chronic fatigue immune dysfunction syndrome (CFIDS) (DeFreitas et al, *Proc. Natl. Acad. Sci. USA* 88:2922–2926,1991) and an HTLV II virus has been isolated from cultured T cells of a patient with pancytopenia (Kalyanaraman et al, *The EMBO Journal* 4:6:1455–1460, 1985). The epidemiology of HTLV II infections is also distinct, being primarily associated with intravenous drug abuse and a focus of HTLV II endemicity has been reported among the native Guaymi Indians of Panama (Heneine et al, 1991, *New Eng. J. Med.* 324:565).

There is no viremia throughout the course of infection with HTLV I or II, i.e., the circulating viral genome (i.e., RNA) cannot be detected. Polymerase chain reaction (PCR) has been shown to be capable of detecting proviral sequences and to distinguish between HTLV I and HTLV II proviruses (Tuke et al., *J. Virological Methods,* 40:163–174, 1992). While it is possible to detect the integrated provirus, it has been difficult to detect mRNA and therefore determine the role of viral gene expression in development and maintenance of the disease state. Screening of patient PBMC by RT/PCR has been used for the detection of the HTLV I tax transcript in the PBMC of asymptomatic patients as well as infected individuals displaying disease, but this assay did not detect HTLV II transcripts (Breneman et al, PNAS 89:3005–3009, 1992).

In view of the very different prognoses associated with HTLV I and HTLV II infection, it is important to be able to distinguish between the two viruses for the purposes of screening of blood donors, epidemiological studies, and routine clinical practice. Serological tests have been attempted, but because of high amino acid sequence homology, such tests have not been able to differentiate the two viruses with certainty (Kline et al, 1991, *Lancet* 337:30–33).

An isothermal amplification method for the detection of HTLV RNAs has not been described. The isothermal method of the present invention for HTLV I and II provides an effective method of screening for the presence of several viral transcripts or viral genome and is able to distinguish between the two viruses.

SUMMARY OF THE INVENTION

The present invention provides isothermal transcription based amplification assays for the detection of HTLV I and HTLV II viral RNAs. The detection assays use primer pairs and probes for each of two target regions in the tax gene, one target in the pol gene, and one target in the gag gene of HTLV I, and primer pairs and probes for each of two target regions in the tax gene of HTLV II. In an HTLV I NASBA assay, tax, pol and gag transcripts were detected from patient peripheral blood mononuclear cells (PBMCS) and in an HTLV II NASBA assay, tax transcripts were detected from the same cells.

An isothermal amplification method starts with an RNA template and alternately synthesizes DNA and RNA. Using an RNA template, reverse transcriptase, and an oligonucleotide (referred to herein as a primer), an RNA/DNA hybrid is generated. The RNA is degraded from the hybrid by the RNAse H activity. A double stranded DNA is then generated by the reverse transcriptase using another oligonucleotide (referred to herein as primer), and then the double stranded DNA is used as template for large amounts of RNA synthesis by the RNA polymerase. One of the primers has, in addition to the sequences complementary to the template, additional sequences necessary for generating an RNA polymerase promoter and transcription initiation site which can be used by the RNA polymerase.

One of the advantages of an isothermal transcription based amplification method, as compared to other amplification methods such as PCR, is that by being isothermal, it requires few manipulations by the experimenter. The method may be used on purified or semi-purified RNA extracts, or on cell or tissue samples with in situ amplification. In addition, if the sample contains both DNA and RNA, the use of the alternative procedure of RT/PCR requires a first step of DNAse treatment, or some method to distinguish the mRNA- and DNA-derived PCR products is necessary. DNAse treatment prior to RT-PCR can be employed (Bitsch, A. et al., *J. Infect Dis.* 167, 740–743, 1993; Meyer, T. et al., *Mol. Cell Probes,* 8, 261–271, 1994), but sometimes fails to remove contaminating DNA sufficiently (Bitsch, A. et al., 1993).

The purpose of applying such an assay would be to determine the presence and level of these transcripts, and to use these levels for the purpose of screening of blood donors, epidemiological studies, and in clinical practice for prognosis and/or therapeutic management.

DETAILED DESCRIPTION OF THE INVENTION

An isothermal transcription based assay is used for the detection of HTLV I and HTLV II viral RNA. Any isothermal transcription based assay may be used with the primers and probes of the present invention. The isothermal transcription based assay of the present invention is carried out under conditions that can be readily determined by a person of ordinary skill in the art.

The preferred amplification method of the present invention is the isothermal transcription based amplification system referred to as NASBA. The NASBA method is disclosed in U.S. Pat. Nos. 5,409,818 and 5,554,527, which are herein incorporated by reference. NASBA includes the use of T7 RNA polymerase to transcribe multiple copies of RNA from a template including a T7 promoter.

Another technique for the amplification of nucleic acid is the so-called transcription based amplification system (TAS). The TAS method is described in International Patent Application No. WO 88/10315. Transcription based amplification techniques usually comprise treating target nucleic acid with two oligonucleotides one of which comprises a promoter sequence, to generate a template including a functional promoter. Multiple copies of RNA are transcribed from said template and can serve as a basis for further amplification.

Other transcription based amplification techniques are described in EP 408295. EP 408295 is primarily concerned with a two-enzyme transcription based amplification method. Transcription based amplification methods, such as the NASBA method described in EP 329822, are usually employed with a set of oligonucleotides, one of which is provided with a promoter sequence that is recognized by an enzyme with DNA dependent RNA polymerase activity such as, for example, T7 polymerase. Several modifications of transcription based techniques are known in the art. These modifications comprise, for example, the use of blocked oligonucleotides (that may be provided with a promoter sequence). These oligos are blocked so as to inhibit an extension reaction proceeding therefrom (U.S. Pat. No. 5,554,516). One or more "promoter-primers" (oligonucleotides provided with a promoter sequence) may be used in transcription based amplification techniques, optionally combined with the use of one or more oligonucleotides that are not provided with a promoter sequence.

The term "oligonucleotide" as used herein refers to a molecule comprised of two or more deoxyribonucleotides or ribonucleotides. Such oligonucleotides may be used as primers and probes.

Of course, based on the sequences of the oligonucleotides of the present invention, analogues of oligonucleotides can also be prepared. Such analogues may comprise alternative structures such as "PNA" (molecules with a peptide-like backbone instead of the phosphate sugar backbone of normal nucleic acid) or the like.

The term "primer" as used herein refers to an oligonucleotide which is capable of acting as a point of initiation of synthesis of a primer extension product which is complementary to a nucleic acid strand (template or target sequence) when placed under suitable conditions (e.g., buffer, salt, temperature and pH) in the presence of nucleotides and an agent for nucleic acid polymerization, such as DNA dependent or RNA dependent polymerase. A primer must be sufficiently long to prime the synthesis of extension products in the presence of an agent for polymerization. A typical primer contains at least 10 nucleotides in length of a sequence substantially complementary to the target sequence, but somewhat longer primers are preferred. Usually primers contain about 15–26 nucleotides but longer primers may also be employed, especially when the primers contain additional sequences such as a promoter sequence for a particular polymerase. Primers may also contain linker sequences between the promoter sequence and the sequences complementary to the target sequence.

Normally a set of primers will consist of at least two primers, one "upstream" (P2) and one "downstream" (P1) primer which together define the amplificate (the sequence that will be amplified using said primers). One of the primers is understood to contain, in addition to sequences that will hybridize to the target sequence, sequences which provide promoter activity. Most often the P1 primer will include the promoter sequence.

The term "promoter sequence" defines a region of a nucleic acid sequence that is specifically recognized by an RNA polymerase that binds to a recognized sequence and initiates the process of transcription by which an RNA transcript is produced. In principle, any promoter sequence may be employed for which there is a known and available polymerase that is capable of recognizing the initiation sequence. Known and useful promoters are those that are recognized by certain bacteriophage RNA polymerases such as bacteriophage T3, T7 or SP6. Their function as a primer, e.g., the starting point for an elongation reaction, however, may be blocked, as already mentioned above, or absent in some embodiments of transcription based amplification reactions. A particularly preferred promoter sequence is the sequence of the T7 RNA polymerase promoter, the sequence of which is as follows: AATTCTAATACGACTCACTATAGGG SEQ ID NO:29.

SEQ ID NOs 3, 8, 12, 16, 21, 23, and 26 comprise the sequences of the specific target primer operably linked to the T7 promoter sequence, shown in italics. This makes the sequences especially suitable for use as a downstream primer in a transcription based amplification technique such as NASBA. However, the sequences for the T7 promoter shown in italics may be substituted by sequences of other promoters for use with other RNA polymerases.

A preferred embodiment of the present invention is a combination of two oligonucleotides according to the invention, for use as a set in nucleic acid amplification.

One of the oligonucleotides may serve as an "upstream oligonucleotide", i.e., upstream primer, while the second oligonucleotide serves as a "downstream oligonucleotide", i.e., downstream primer, in the amplification reaction.

Preferably, the reverse transcriptase activity is provided by avian myeloblastosis virus (AMV) reverse transcriptase and the RNA polymerase is provided by T7 RNA polymerase.

One of the advantages of an isothermal transcription based amplification method, as compared to other amplification methods such as PCR, is that by being isothermal, it requires few manipulations by the experimenter. However, the absence of a high temperature step does make it somewhat more difficult to find appropriate primers (see below).

The amplification method of the present invention may be applied to extracts of samples comprising nucleic acid, or whole cells or tissues for in situ amplification. The samples may be various body fluids, particularly blood, plasma, and serum, from humans. The samples may also be tissue samples from humans, for instance, lymph tissue.

If the method is applied to extracts of samples comprising nucleic acids, the sample may be total RNA extracts (such as those described in Chomczynski and Sacchi, *Anal. Biochem.*162:156, 1987 ) or "Boom" extracts (Boom et al, *J. Clin. Micro.:* 28, No.3, March 1990, p.495–503), which is herein incorporated by reference. The method is preferably applied to "Boom extracts".

The amplificate is detected by hybridization with an appropriately labeled oligonucleotide probe. The label may contain a radioactive moiety, a detectable enzyme, or any other moiety capable of generating a detectable signal, such as a colorimetric, fluorescent, chemiluminescent or electrochemiluminescent (ECL) signal. Blot based hybridization analysis and liquid hybridization based ECL analysis are preferably used, although other analysis systems such as ELGA (enzyme-linked gel assay) and in situ hybridization can also be used.

In one embodiment of the present invention, the amplification products are resolved by agarose gel electrophoresis, then transferred to nylon membranes and hybridized to a probe that is 5'-end labeled with $^{32}P$ using standard methods. The products are then visualized by autoradiography.

In a second embodiment of the present invention, the amplification products can be detected using the ELGA. In this method a probe that is specific for the amplification reaction product and conjugated at its 5' end with horseradish peroxidase (HRP) is hybridized to the amplification product. The hybridization product is then resolved electrophoretically on a polyacrylamide gel. A colorimetric enzyme reaction allows for the visualization of the reaction product in the gel.

A third embodiment of the present invention makes use of electrochemiluminescence chemistry (or ECL). This embodiment uses a biotinylated capture probe immobilized onto the surface of a streptavidin-coated magnetic bead via the biotin-avidin interaction. This system also requires an oligonucleotide detector probe, which can hybridize to an independent region of the amplification product. This detector probe is labeled with Ruthenium, the substance that is responsible for generating an ECL signal.

Each of the detection systems could use one or more internal controls to monitor the efficiency of the extraction process and the amplification assay itself. The detection systems are described in detail in Romano et al, *DNA Technology* 16:89–103 (1996), and van Gemen et al., *J. of Virol. Methods,* 49:157–168 (1994), which are herein incorporated by reference. Methods for internal controls are described in van Gemen et al, *Reviews in Medical Virology,* 5:205–211 (1995), which is herein incorporated by reference.

It may also be relevant to adapt the assay for an in situ format, which would be useful in pathology studies of tissue, particularly for lymphatic tissues. If the method is to be practiced on fixed preparations for in situ analysis, the method is performed as follows. The cells are fixed and then permeabilized to optimize permeability of the cell membranes. The fixatives are those standardly used in the art for cell or tissue preparations, such as acetone and methanol, ethanol, formalin, formaldehyde, paraformaldehyde, or Permafix®, and the permeabilization is done by proteinases, such as proteinase K or pepsinogen. The cells are then washed to remove all reagents that might inhibit the transcription based reaction. Permeabilization is done to the point that the cells allow entry of all necessary amplification reaction components, yet retain the targets and amplification products within the cells. In addition, cosolvents such as glycerol or DMSO may be added to optimize the NASBA reaction.

Detection of amplification products may be by direct labelling (with, for instance, biotin or digoxigenin—UTP) or by in situ hybridization with labelled probe. The direct labelling method requires that conditions can be optimized to remove unincorporated label while maintaining the amplification products.

In a particularly preferred embodiment of the present invention, the isothermal transcription based amplification method is used in concert with a particular RNA extraction technique ("Boom extraction", Boom et al, *J. Clin. Micro.:* 28, No.3, March 1990, p.495–503), and ECL detection (electrochemiluminescence). The advantages of the system are those associated with an amplification based assay capable of providing sequence level data. Although some of these same advantages exist for the RT-PCR (i.e., increased sensitivity over ELISA, gene sequence specificity), there are advantages of NASBA for RNA over RT-PCR. These include isothermal amplification, incorporation of reverse transcription into the amplification process, generation of a single-stranded product for purposes of detection by hybridization, application to wider array of specimen types (via Boom extract), and the sensitivity and dynamic range of the ECL detection.

Boom extracts are purified preparations of DNA and RNA. The Boom method is based on the lysing and nuclease inactivating properties of the chaotropic agent guanidinium thiocyanate (GuSCN) together with the nucleic acid binding properties of silica particles or diatoms. By using size fractionated silica particles, nucleic acids, including covalently closed circular, relaxed circular, linear double-stranded DNA, single stranded DNA, tRNA, mRNA, and rRNA, can be purified from a sample in less than one hour and recovered in the original reaction vessel.

A small sample is pipetted into a reaction vessel containing a solid nucleic acid carrier and a GuSCN containing lysis buffer. Lysis of the cells occurs and the released nucleic acids bind to the carrier. The carrier-nucleic acid complexes can be separated by centrifugation. Several wash steps follow and the complexes are then dried. The nucleic acids are eluted in an aqueous low-salt buffer in the initial reaction vessel and used for the amplification reaction.

In a preferred embodiment of the present invention, amplification is achieved in a 20 $\mu$L reaction containing 5 $\mu$L of the nucleic acid extract material in 10 $\mu$L of premix [Tris (40 mM) pH8.5; $MgCl_2$(12 mM); KCL (70 mM); DTT (5mM); dNTPs (each) (1 mM); rATP, rUTP, rCTP (2 mM); rGTP (1.5 mM); ITP (0.5 mM); DMSO (15%); P1 and P2, (0.2 $\mu$M); Sorbitol (1.5 M)]. This is then added to 5 $\mu$L of enzyme mix [BSA (2.1 $\mu$g/NASBA); RNase H (0.08 unit/NASBA); T7 RNA Polymerase (32 units/NASBA); and AMV-RT (6.4 units/NASBA)]. (The enzyme mixture must not be vortexed). If the nucleic acid sample decreases (5 $\mu$l), then the water volume increases accordingly so that the total volume stays 15 $\mu$l when the nucleic acid is added.

(It has been determined that the preferred method of the invention for the detection of the HTLV I gag transcript uses a premix with 42 mM KCL, rather than the 70 mM KCL preferred for the other targets and primer sets.)

The method can be carried out as follows.

1. Mix premix.
2. Add 10 $\mu$l of premix to 5 $\mu$l of nucleic acid in an Eppendorf tube.
3. Incubate at 65° C. for 5 minutes.
4. Transfer to 41° C. heat block, incubate for 5 minutes.
5. Add 5 $\mu$l of enzyme mix.
6. Mix without vortexing.
7. Incubate at 41° C. for 5 minutes.
8. If the tops of the tubes have condensation from the cooling, they may be spun.
9. Incubate at 41° C. for 90 minutes.
10. Spin down samples and store at −20° C.

In the method of the present invention primers and probes were designed for the transcripts of the tax, pol, and gag genes of HTLV I and the tax gene of HTLV II.

The primer and probe sequences were derived from the Genbank and/or Los Alamos data base for retroviruses entries for these genes.

The primer and probe oligonucleotides are listed on Tables 1 and 2.

TABLE 1

HTLV-I Oligonucleotides

| Oligo | (Map Site*) | Sequence (all listed 5' to 3') |
|---|---|---|
| HTLV I tax A | | |
| P2A | (7372-7396) | ACGTGTTTGGAGACTGTGTACAAGG SEQ ID NO:1 |
| P1A | (7522-7543) | AGTCGAGGGATAAGGAACTGTA SEQ ID NO:2 |
| P1A* | | AATTCTAATACGACTCACTATAGGGAGTCGAGGGATAAGGAACTGTA SEQ ID NO:3 |
| DETECTION PROBE | (7426-7450) | GTTCGGCCCGCCTACATCGTCACGC SEQ ID NO:4 |
| CAPTURE PROBE | (7485-7509) | TGGGACCCCATCGATGGACGCGTTA SEQ ID NO:5 |
| HTLV I tax B | | |
| P2A | (7828-7852) | ACGTGATTTTTTGCCACCCCGGCCA SEQ ID NO:6 |
| P1A | (8007-8031) | GGAACGGAAGGAGGCCGTTTTGCCA SEQ ID NO:7 |
| P1A* | | AATTCTAATACGACTCACTATAGGGGGAACGGAAGGAGGCCGTTTTGCCA SEQ ID NO:8 |
| DETECTION PROBE | (7925-7949) | AGGGGCCCTAATAATTCTACCCGAA SEQ ID NO:9 |
| HTLV I pol | | |
| P2A | (4724-4752) | ACCTCCCTTGCTATTCGCCATACCACCCA SEQ ID NO:10 |
| P1A | (4953-4981) | GAGGGAACGTGTCTCTGGGATCGGCTGGA SEQ ID NO:11 |
| P1A* | | AATTCTAATACGACTCACTATAGGGGAGGGAACGTGTCTCTGGGATCGGCTGGA SEQ ID NO:12 |
| DETECTION PROBE | (4883-4907) | ACAATCAACCACCTGAATGTGTTAA SEQ ID NO:13 |
| HTLV I gag | | |
| P2A | (1263-1287) | TGAAAGACCTACAGGCCATTAAGCA SEQ ID NO:14 |
| P1A | (1386-1406) | AGGAGCAAAGGTACTGCAGGA SEQ ID NO:15 |
| P1A* | | AATTCTAATACGACTCACTATAGGGAGGAGCAAAGGTACTGCAGGA SEQ ID NO:16 |
| DETECTION PROBE | (1352-1375) | CAGTTTGACCCCAC(T/C)GCCAA(A/G)GAC SEQ ID NO:17 |

(the bases in parentheses represent mixed sites)

TABLE 2

HTLV II Oligonucleotides

| Oligo | (Map Site*) | Sequence (all listed 5' to 3') |
|---|---|---|
| HTLV II tax A | | |
| P2A | (7248-7267) | TGGATACCCCGTCTACGTGT SEQ ID NO:18 |
| P2B | (7269-7288) | TGGCGATTGTGTACAGGCCG SEQ ID NO:19 |
| P1A | (7368-7387) | CGATGGGGTCCCAGGTGAGT SEQ ID NO:20 |
| P1A* | | AATTCTAATACGACTCACTATAGGGCGATGGGGTCCCAGGTGAGT SEQ ID NO:21 |
| P1B | (7390-7407) | AGAGCTGACAACGCGTCC SEQ ID NO:22 |
| P1B* | | AATTCTAATACGACTCACTATAGGGAGAGCTGACAACGCGTCC SEQ ID NO:23 |
| PROBE | (7316-7340) | GTTCCACCCGCCTACATCGACATGC SEQ ID NO:24 |

TABLE 2-continued

| Oligo | (Map Site*) | Sequence (all listed 5' to 3') |
|---|---|---|
| HTLV II tax B | | |
| P1 | (7840-7864) | GGAACATTGTGGTGGGTAGGTCGTC SEQ ID NO:25 |
| P1A* | | AATTCTAATACGACTCACTATAGGGAGAGGGAACATTGTGGTGGGTAGGTCGTC SEQ ID NO:26 |
| P2 | (7658-7682) | CCGTAGTATGCCTATACCTATACCA SEQ ID NO:27 |
| PROBE | (7801-7825) | ATGTTCCTACACACAGGGACAGTCA SEQ ID NO:28 |

*Position 1 is the first base in the genomic map of each virus.

Example 1—Initial Evaluation of Oligonucleotides

A. Sensitivity Evaluation

The primer sets shown on Tables 1 and 2 were used in the following experiments. The primer set used for HTLV II tax A was set P2B/P1B in examples below.

Sensitivity was assessed for each primer set by determining (1) the lowest number of chronically infected cells that are detectable, and (2) the least amount of total RNA obtained from chronically infected cell lines that is detectable.

For the cell sensitivity experiments, nucleic acids were extracted by the Boom method and amplification was by the standard NASBA method disclosed above using the indicated primer sets. Detection was by blot based $^{32}P$ detection outline above.

For the total RNA sensitivity experiments, RNA was extracted by the Chomczynski and Sacchi method and amplification was by the standard NASBA method disclosed above using the indicated primer sets. Detection was by blot based $^{32}P$ detection outline above.

The results are summarized in Tables 3 and 4, respectively.

TABLE 3

CELL SENSITIVITY

| Primer Set | Cell Equivalent MT2 | Cell Equivalent MoT |
|---|---|---|
| HTLV I tax A | 0.4 cells | – |
| HTLV I tax B | 40 cells | – |
| HTLV I pol | 40 cells | – |
| HTLV I gag | ND | ND |
| HTLV II tax A | – | 5 cells |
| HTLV II tax B | – | 50 cells |

– negative at 4000 cells for MT2 and at 5000 cells for MoT

*A1 ml aliquot of MT2 ($8 \times 10^5$ cells/ml) and MoT ($1 \times 10^6$ cells/ml) were lysed in 9 mls GuSCN lysis buffer pH 6.8. The Boom extraction method was used to isolate the nucleic acid, using 70 ul silica and eluting in 100 ul of $dH_2O$.

TABLE 4

TOTAL RNA SENSITIVITY

| Primer Set | MT2 | MoT |
|---|---|---|
| HTLV I tax A | 5 pg | – |
| HTLV I tax B | 500 pg | – |
| HTLV I pol | 5 ng | – |

TABLE 4-continued

TOTAL RNA SENSITIVITY

| Primer Set | MT2 | MoT |
|---|---|---|
| HTLV I gag | 500 pg | – |
| HTLV II tax A | – | 50 pg |
| HTLV II tax B | – | 50 pg |

– negative at 5 ng MoT

Results from this analysis indicate that the greatest sensitivity among the HTLV I primer sets was achieved with the HTLV I tax A primers. This finding was confirmed at the cellular as well as the RNA levels. However, it should be noted that these experiments were conducted with extracts from chronically infected cells and the apparent sensitivity could simply be a reflection of specific tax transcript expression in those cells. The two primer sets developed for HTLV II were for different sites within the tax gene. Interestingly, the tax A and B primer sets were not equally sensitive, suggesting a specific target sequence effect on sensitivity. Cell sensitivity experiments indicated that fewer cells are detectable with the HTLV II tax A primers, however total RNA results were the same for both primer sets. Therefore there is probably very little difference in the sensitivity capabilities of these two HTLV II tax primer sets.

B. Specificity

Specificity experiments were conducted using a constant amount of total RNA obtained from different cell lines that were chronically infected with various retroviruses.

For the cell specificity experiments, nucleic acids were extracted by the Boom method and amplification was by the standard NASBA method disclosed above using the indicated primer sets. Detection was by blot based $^{32}P$ detection outline above. The nucleic acid equivalent from $4 \times 10^4$ cells went into each amplification reaction.

For the total RNA specificity experiments, RNA was extracted by the Chomczynski and Sacchi method and amplification was by the standard NASBA method disclosed above using the indicated primer sets. 5 ng Total RNA/rxn was used. Detection was by blot based $^{32}P$ detection outline above.

The results are shown on Tables 5 and 6.

TABLE 5

CELL SPECIFICITY

| Primer Set | MT2 | MoT | H9 + | H9 − | silica extraction of cells WATER |
|---|---|---|---|---|---|
| HTLV I tax A Elga only | + | − | − | − | − |
| HTLV I* tax B | +/− | − | − | − | − |
| HTLV I pol A | + | − | − | − | − |
| HTLV I gag | ND | ND | ND | ND | ND |
| HTLV II tax A | − | + | − | − | − |
| HTLV II tax B | − | + | − | − | − |
| HIV-1 gag-3 Elga only | − | − | − | + | − |

Note: Used 5 ul of $8 \times 10^3$/ul MT2 cell equivalents and 4 ul of $1 \times 10^4$/ul cell equivalents MoT, H9+, and H9−; all detections by $^{32}P$ labeled probe except where noted
*poor amplification trial
+ is positive, − is negative, and −/+ is weakly positive

TABLE 6

TOTAL RNA SPECIFICITY

| Primer Set | MT2 | MoT | NS-1 | H9+ | H9− | WATER |
|---|---|---|---|---|---|---|
| HTLV I tax A | + | − | + | − | − | − |
| HTLV I tax B | + | − | + | − | − | − |
| HTLV I pol A | + | − | − | − | − | − |
| HTLV I gag | ND | ND | ND | ND | ND | ND |
| HTLV II tax A | +* | + | − | − | − | − |
| HTLV II tax B | ND | ND | ND | ND | ND | ND |
| HIV-1 gag-3 ELGA | − | − | − | + | − | − |

Note: All detections by $^{32}P$ labeled probe except where noted
*Very weakly positive
+ is positive, − is negative, and −/+ is weakly positive A high degree of specificity was exhibited by all of the HTLV I primer sets using total RNA (5 ng/rxn) as well as cell extracts. However, variable results were obtained with the HTLV II primer sets. Although the HTLV II tax B primer set exhibited specific reactivity, there was evidence of cross reactivity with the HTLV II tax A primers.

Example 2—Testing of Patient Samples

Clinical samples were examined with the methods of the present invention. Initially, PBMCs from 20 primary cultures were obtained from various HTLV I/HTLV II infected patients. These materials were collected and cryopreserved several years ago without regard for future analysis by amplification methodologies (The integrity of the RNA was confirmed by sn-RNP NASBA analysis). Boom RNA extractions of the samples were then tested with the HTLV I tax A primer set. Detection of the amplification products were by hybridization with $^{32}P$, ELGA, or $Ru^{2+}$. The results are shown in Table 7.

TABLE 7

| Patent ID | NSUH | NASBA HTLV I | Disease |
|---|---|---|---|
| Ca* | HTLV I | −/+ | asympto. |
| Gas | HTLV I | + | ATL |
| La | HTLV I | + | TSP/HIV-1 |
| Fl | HTLV I | + | ATL |
| Che | HTLV I | −/+ | CLL |
| Do | HTLV I | + | ATL |
| Sp** | HTLV I | − | TSP |
| Ba | HTLV I | + | asympto. |
| Ha | HTLV I | + | CLL/HIV-1 |
| Re | HTLV I | + | asympto. |
| L78 | HTLV I | + | asympto. |
| L97 | HTLV I | + | asympto |
| Da | HTLV II | + | none |
| Fly | HTLV II | −/+ | none |
| Gar | HTLV II | + | HIV-1 |
| Fu | HTLV II | − | none |
| St | HTLV II | − | HIV-1 |
| Cha | HTLV II | − | HIV-1 |
| Pa | HTLV II | − | none |
| We | HTLV II | − | HIV-1 |

*Patient Ca was originally diagnosed as HTLV I infected, but there is reason to believe that this patient may actually be HTLV II positive
**Patient Sp was negative for sn-RNP RNA; all other samples were positive for this control of RNA quality.
+ is positive, − is negative, and −/+ is weakly positive The results indicated that all of the HTLV I positive patients were positive by HTLV I tax A NASBA.

Further, all except three of the HTLV II positive patients were negative with the HTLV I tax A primer set. It was suspected that the positive results obtained with the HTLV II samples were due to contamination of the original sample material. Experiments with chronically infected cell lines failed to show cross reactivity, and the level of HTLV II RNA is assumed to be high in such cell lines.

Nine additional samples from the same patient set were then obtained. Seven of the nine were positive for sn-RNP NASBA, and were the ones used for additional experiments. Of these seven, only one tested positive for HTLV I using the tax A primer set and probe (data not shown). This was the only sample of the seven which was previously known to be HTLV I positive.

Some of the samples from the original 20 patient specimens were then tested with some of the other primer sets developed in the present invention. Boom RNA extracts of these samples were tested in the standard NASBA assay. These results are shown on Table 8.

Excellent specificity was demonstrated for each for the HTLV I primer sets. Two of the HTLV II specimens in the original group which were shown to be HTLV I tax A positive were included in subpanel 2. These samples were negative in this repeat analysis with the HTLV I tax A primer set.

These experiments also demonstrated that each of the RNA analytes targeted by the individual primer sets could be used to detect viral RNA in patient samples. It appears that the HTLV II tax B primer set may have higher specificity.

TABLE 8

PATIENT PANEL STUDY

| | Fl I | Fu II | Ha I | Re I | We II | Da II | Gar II | La I | Vi II |
|---|---|---|---|---|---|---|---|---|---|
| HTLVI tax A | + | − | + | + | − | − | − | + | − |
| HTLVI | + | − | + | + | − | − | − | + | − |

TABLE 8-continued

| | PATIENT PANEL STUDY | | | | | | | | |
|---|---|---|---|---|---|---|---|---|---|
| | Fl I | Fu II | Ha I | Re I | We II | Da II | Gar II | La I | Vi II |
| tax B HTLVI pol | + | − | + | + | − | − | − | + | − |
| HTLVI gag | ND | ND | ND | ND | ND | ND | ND | ND | ND |
| HTLVII tax A | + | + | + | + | + | − | + | − | + |
| HTLVII tax B | ND | ND | ND | ND | ND | −, +" | +, −" | −, −" | +, +" |

*Results from duplicate analysis due to poor assay performance

The biggest problem encountered in the development of NASBA assays is the selection of primers. It has often been the case that primers selected from sequence data, and meeting all the known requirements for primers, do not actually function in practice. In addition, in some cases primers have been developed using model systems such as in vitro transcribed RNA, virus stocks, or cells lines with very high expression of the target gene, but those primers were found to be nonfunctional when the target molecule is in a background of clinical samples. The exact mechanism underlying this problem is not understood, but is believed to arise due to the lower temperature of the NASBA reaction, which does not entirely melt secondary structure of the target molecule and/or allows nonspecific binding of primers to background nucleic acids in the sample. It is essential for the application of the NASBA system to clinical samples that the primers not be absorbed by background nucleic acids, but rather be available for specific binding to the target molecule.

The HTLV I tax A primer set was able to amplify 5 pg of total RNA from these cells; the tax B and pol primers were able to amplify down to 500 pg and 5 ng, respectively. The difference in sensitivity for the two tax primer sets, which are specific for the same RNA molecule, indicates a primer based component to NASBA sensitivity. This is most likely due to secondary structure issues which are typical with RNA analytes. Despite the fact that the same number of target molecules are present for the tax A and B primer sets, the two sets of primers may not be able to anneal to their respective targets with equal efficiency.

Even though the non-preferred primers of the present invention are non-preferred for a NASBA method, such primers may be useful for other amplification methods such as polymerase chain reaction (PCR) or reverse transcription/polymerase chain reaction (RT/PCR).

SEQUENCE LISTING

```
(1) GENERAL INFORMATION:

   (iii) NUMBER OF SEQUENCES: 28


(2) INFORMATION FOR SEQ ID NO:1:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (ii) MOLECULE TYPE: DNA

    (xi) SEQUENCE DESCRIPTION: SEQ ID NO:1:

ACGTGTTTGG AGACTGTGTA CAAGG                                          25


(2) INFORMATION FOR SEQ ID NO:2:

     (i) SEQUENCE CHARACTERISTICS:
          (A) LENGTH: 22 base pairs
          (B) TYPE: nucleic acid
          (C) STRANDEDNESS: single
          (D) TOPOLOGY: linear

    (ii) MOLECULE TYPE: DNA

    (xi) SEQUENCE DESCRIPTION: SEQ ID NO:2:

AGTCGAGGGA TAAGGAACTG TA                                             22


(2) INFORMATION FOR SEQ ID NO:3:

     (i) SEQUENCE CHARACTERISTICS:
          (A) LENGTH: 47 base pairs
          (B) TYPE: nucleic acid
          (C) STRANDEDNESS: single
          (D) TOPOLOGY: linear
```

(ii) MOLECULE TYPE: DNA (xi) SEQUENCE DESCRIPTION: SEQ ID NO:3:

AATTCTAATA CGACTCACTA TAGGGAGTCG AGGGATAAGG AACTGTA 47

(2) INFORMATION FOR SEQ ID NO:4:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:4:

GTTCGGCCCG CCTACATCGT CACGC 25

(2) INFORMATION FOR SEQ ID NO:5:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:5:

TGGGACCCCA TCGATGGACG CGTTA 25

(2) INFORMATION FOR SEQ ID NO:6:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:6:

ACGTGATTTT TTGCCACCCC GGCCA 25

(2) INFORMATION FOR SEQ ID NO:7:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:7:

GGAACGGAAG GAGGCCGTTT TGCCA 25

(2) INFORMATION FOR SEQ ID NO:8:

(i) SEQUENCE CHARACTERISTICS:
(A) LENGTH: 50 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

AATTCTAATA CGACTCACTA TAGGGGGAAC GGAAGGAGGC CGTTTTGCCA 50

(2) INFORMATION FOR SEQ ID NO:9:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:9:

AGGGGCCCTA ATAATTCTAC CCGAA 25

(2) INFORMATION FOR SEQ ID NO:10:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:10:

ACCTCCCTTG CTATTCGCCA TACCACCCA 29

(2) INFORMATION FOR SEQ ID NO:11:

(i) SEQUENCE CHARACTERISTICS:
(A) LENGTH: 29 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

GAGGGAACGT GTCTCTGGGA TCGGCTGGA 29

(2) INFORMATION FOR SEQ ID NO:12:

(i) SEQUENCE CHARACTERISTICS:
(A) LENGTH: 54 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:12:

AATTCTAATA CGACTCACTA TAGGGGAGGG AACGTGTCTC TGGGATCGGC TGGA 54

(2) INFORMATION FOR SEQ ID NO:13:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:13:

ACAATCAACC ACCTGAATGT GTTAA 25

(2) INFORMATION FOR SEQ ID NO:14:

(i) SEQUENCE CHARACTERISTICS:

(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:14:

TGAAAGACCT ACAGGCCATT AAGCA 25

(2) INFORMATION FOR SEQ ID NO:15:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:15:

AGGAGCAAAG GTACTGCAGG A 21

(2) INFORMATION FOR SEQ ID NO:16:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:16:

AATTCTAATA CGACTCACTA TAGGGAGGAG CAAAGGTACT GCAGGA 46

(2) INFORMATION FOR SEQ ID NO:17:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:17:

CAGTTTGACC CCACYGCCAA RGAC 24

(2) INFORMATION FOR SEQ ID NO:18:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:18:

TGGATACCCC GTCTACGTGT 20

(2) INFORMATION FOR SEQ ID NO:19:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:19:

TGGCGATTGT GTACAGGCCG 20

(2) INFORMATION FOR SEQ ID NO:20:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:20:

CGATGGGGTC CCAGGTGAGT 20

(2) INFORMATION FOR SEQ ID NO:21:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:21:

AATTCTAATA CGACTCACTA TAGGGCGATG GGGTCCCAGG TGAGT 45

(2) INFORMATION FOR SEQ ID NO:22:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:22:

AGAGCTGACA ACGCGTCC 18

(2) INFORMATION FOR SEQ ID NO:23:

(i) SEQUENCE CHARACTERISTICS:
(A) LENGTH: 43 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:23:

AATTCTAATA CGACTCACTA TAGGGAGAGC TGACAACGCG TCC 43

(2) INFORMATION FOR SEQ ID NO:24:

(i) SEQUENCE CHARACTERISTICS:
(A) LENGTH: 25 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:24:

GTTCCACCCG CCTACATCGA CATGC 25

```
(2) INFORMATION FOR SEQ ID NO:25:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (ii) MOLECULE TYPE: DNA

    (xi) SEQUENCE DESCRIPTION: SEQ ID NO:25:

GGAACATTGT GGTGGGTAGG TCGTC                                          25


(2) INFORMATION FOR SEQ ID NO:26:

     (i) SEQUENCE CHARACTERISTICS:
          (A) LENGTH: 54 base pairs
          (B) TYPE: nucleic acid
          (C) STRANDEDNESS: single
          (D) TOPOLOGY: linear

    (ii) MOLECULE TYPE: DNA

    (xi) SEQUENCE DESCRIPTION: SEQ ID NO:26:

AATTCTAATA CGACTCACTA TAGGGAGAGG GAACATTGTG GTGGGTAGGT CGTC          54


(2) INFORMATION FOR SEQ ID NO:27:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (ii) MOLECULE TYPE: DNA

    (xi) SEQUENCE DESCRIPTION: SEQ ID NO:27:

CCGTAGTATG CCTATACCTA TACCA                                          25


(2) INFORMATION FOR SEQ ID NO:28:

     (i) SEQUENCE CHARACTERISTICS:
          (A) LENGTH: 25 base pairs
          (B) TYPE: nucleic acid
          (C) STRANDEDNESS: single
          (D) TOPOLOGY: linear

    (ii) MOLECULE TYPE: DNA

    (xi) SEQUENCE DESCRIPTION: SEQ ID NO:28:

ATGTTCCTAC ACACAGGGAC AGTCA                                          25
```

We claim:

1. An oligonucleotide of 10–50 nucleotides, comprising at least 10 consecutive nucleotides of a sequence selected from the group consisting of SEQ ID NO:1 , SEQ ID NO:2, SEQ ID NO:4, SEQ ID NO:5, SEQ ID NO:6, SEQ ID NO:7, SEQ ID NO:9, SEQ ID NO:10, SEQ ID NO:11, SEQ ID NO:13, SEQ ID NO:14, SEQ ID NO:15, SEQ ID NO:17, SEQ ID NO:18, SEQ ID NO:19, SEQ ID NO:20, SEQ ID NO:22, SEQ ID NO:24, SEQ ID NO:25, SEQ ID NO:27, and SEQ ID NO:28,

2. An oligonucleotide comprising the oligonucleotide of claim 1 further comprising the sequence of SEQ ID NO:29 at the 5' end thereof.

3. A method for the detection of HTLV I RNA in a sample, comprising:

a) obtaining a sample which may contain HTLV I RNA;

b) performing isothermal transcription based amplification on the sample with 2 oligonucleotide primers, one of which comprises at least 10 consecutive nucleotides of a sequence selected from the group consisting of SEQ ID NO:2, SEQ ID NO:3, SEQ ID NO:7, SEQ ID NO:8, SEQ ID NO:11, SEQ ID NO:12, SEQ ID NO:15, and SEQ ID NO:16, and the other of which comprises at least 10 consecutive nucleotides of a sequence selected from the group consisting of SEQ ID NO:1, SEQ ID NO:6, SEQ ID NO:10, and SEQ ID NO:14; and c) detecting the resulting product of step b), whereby detection of the amplification product indicates the presence of HTLV I RNA in the sample.

4. The method of claim 3, wherein the sample comprises cells and RNA is extracted from the cells in the sample prior to step b).

5. The method of claim 3, wherein the detection step uses a labeled probe, wherein the probe comprises a sequence selected from the group consisting of SEQ ID NO:4, SEQ ID NO:5, SEQ ID NO:9, SEQ ID NO:13 and SEQ ID NO:17, whereby hybridization of the probe to the amplification product indicates the presence of HTLV I RNA in the sample.

6. A kit for the detection or quantitation of HTLV I RNA in a sample, comprising two primers selected from the group consisting of SEQ ID NO:2, SEQ ID NO:3, SEQ ID NO:7, SEQ ID NO:8, SEQ ID NO:11, SEQ ID NO:12, SEQ ID NO:15, SEQ ID NO:16, SEQ ID NO:1, SEQ ID NO:6, SEQ ID NO:10, and SEQ ID NO:14.

7. The kit of claim 6 wherein the primers are SEQ ID NO:1 and SEQ ID NO:3.

8. The kit of claim 6 wherein the primers are SEQ ID NO:6 and SEQ ID NO:8.

9. The kit of claim 6 wherein the primers are SEQ ID NO:10 and SEQ ID NO:12.

10. The kit of claim 6 wherein the primers are SEQ ID NO:14 and SEQ ID NO:16.

11. The kit of claim 6 further comprising, disposed in a separate container, a probe comprising a sequence selected from the group consisting of SEQ ID NO:4, SEQ ID NO:5, SEQ ID NO:9, SEQ ID NO:13 and SEQ ID NO:17.

12. The kit of claim 6 wherein the primers are SEQ ID NO:18 and SEQ ID NO:23.

13. The kit of claim 6 wherein the primers are SEQ ID NO:19 and SEQ ID NO:23.

14. The kit of claim 6 wherein the primers are SEQ ID NO:26 and SEQ ID NO:27.

15. A method for the detection of HTLV II RNA in a sample, comprising:

a) obtaining a sample which may contain HTLV II RNA;

b) performing isothermal transcription based amplification on the sample with 2 oligonucleotide primers, one of which comprises at least 10 consecutive nucleotides of a sequence selected from the group consisting of SEQ ID NO:20, SEQ ID NO:21, SEQ ID NO:22, SEQ ID NO:23, SEQ ID NO:25, and SEQ ID NO:26 and the other of which comprises at least 10 consecutive nucleotides of a sequence selected from the group consisting of SEQ ID NO:18, SEQ ID NO:19, and SEQ ID NO:27; and c) detecting the resulting product of step b), whereby detection of the amplification product indicates the presence of HTLV II RNA in the sample.

16. The method of claim 15, wherein the sample comprises cells and RNA is extracted from the cells in the sample prior to step b).

17. The method of claim 15, wherein the detection step uses a labeled probe, wherein the probe comprises a sequence selected from the group consisting of SEQ ID NO:24 and SEQ ID NO:28, whereby hybridization of the probe to the amplification product indicates the presence of HTLV II RNA in the sample.

18. A kit for the detection or quantitation of HTLV II RNA in a sample, comprising two primers selected from the group consisting of SEQ ID NO:20, SEQ ID NO:21, SEQ ID NO:22, SEQ ID NO:23, SEQ ID NO:25, SEQ ID NO:26 SEQ ID NO:18, SEQ ID NO:19, and SEQ ID NO:27.

19. The kit of claim 18 wherein the primers are SEQ ID NO:18 and SEQ ID NO:21.

20. The kit of claim 18 wherein the primers are SEQ ID NO:19 and SEQ ID NO:21.

21. The kit of claim 18 further comprising, disposed in a separate container, a probe comprising a sequence selected from the group consisting of SEQ ID NO:24 and SEQ ID NO:28.

* * * * *